Figure 1:
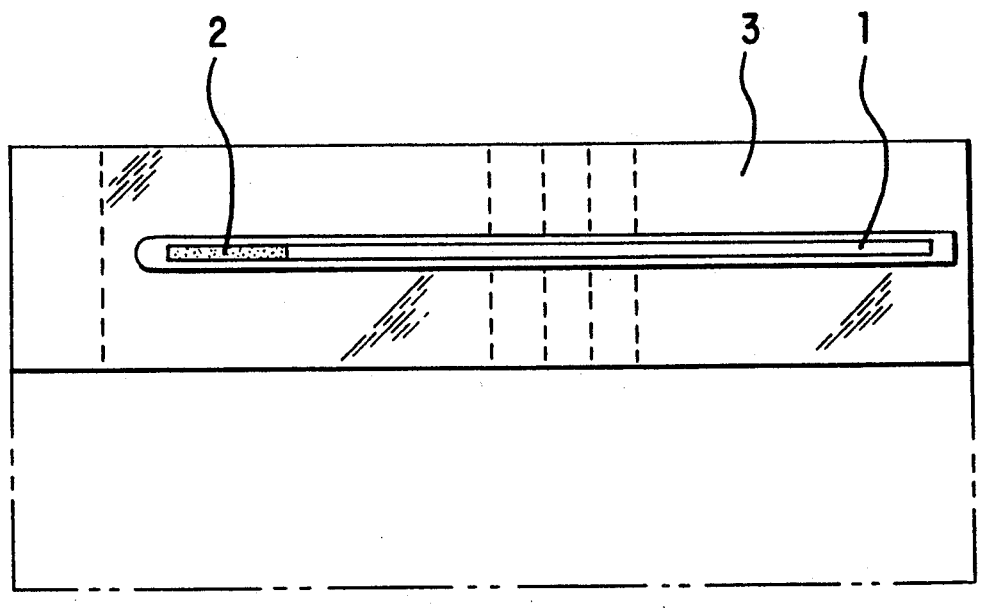

United States Patent [19]

Viljanto et al.

[11] Patent Number: 5,113,871
[45] Date of Patent: May 19, 1992

[54] DEVICE FOR THE DETERMINATION OF INCISIONAL WOUND HEALING ABILITY

[76] Inventors: Jouko Viljanto, Terkokatu 18, SF-20720 Turku; Rainer Govenius, Eristäjänmutka 29, SF-20310 Turku; Kurt Lönnqvist, Uudenmaankatu 12 B, SF-20500 Turku; Timo Hurula, Tuureporinkatu 14 B, SF-20110 Turku, all of Finland

[21] Appl. No.: 457,726
[22] PCT Filed: Jul. 8, 1988
[86] PCT No.: PCT/FI88/00113
  § 371 Date: Mar. 15, 1990
  § 102(e) Date: Mar. 15, 1990
[87] PCT Pub. No.: WO89/00403
  PCT Pub. Date: Jan. 26, 1989

[30] Foreign Application Priority Data
Jul. 13, 1987 [FI] Finland .................... 873075

[51] Int. Cl.⁵ .................................. A61B 5/00
[52] U.S. Cl. .................................... 128/768
[58] Field of Search ............... 128/749, 767, 768, 769, 128/760; 604/318, 327, 328, 282

[56] References Cited

U.S. PATENT DOCUMENTS

| | | | |
|---|---|---|---|
| 1,596,754 | 8/1926 | Moschelle | 604/282 |
| 3,640,268 | 2/1972 | Davis | 128/759 |
| 3,688,763 | 9/1972 | Cromarty | 128/759 |
| 3,957,054 | 5/1976 | McFarlane | 604/282 |

FOREIGN PATENT DOCUMENTS 2713212 10/1977 Fed. Rep. of Germany .
3632303 4/1987 Fed. Rep. of Germany .
2285148 9/1974 France .

OTHER PUBLICATIONS

Viljanto, A., Cellstu: A Device for Wound Healing Studies in Man, Journal of Surgical Research, 20:115-19 (1976), on or before Dec. 1976.

*Primary Examiner*—Max Hindenburg
*Attorney, Agent, or Firm*—Rothwell, Figg, Ernst & Kurz

[57] ABSTRACT

The object of the invention is a device for determining the healing ability of a surgical wound or a connective tissue. A flexible capillary tube (1) is inserted into the wound, the said tube having at the end to be inserted a sponge (2) for the attachment and growth of cells. At least that end of the capillary tube (1) which is left inside the wound is provided with at least one inner groove. The sponge is wet-expanding viscose cellulose sponge containing macro- and micropores in communication with each other.

5 Claims, 4 Drawing Sheets

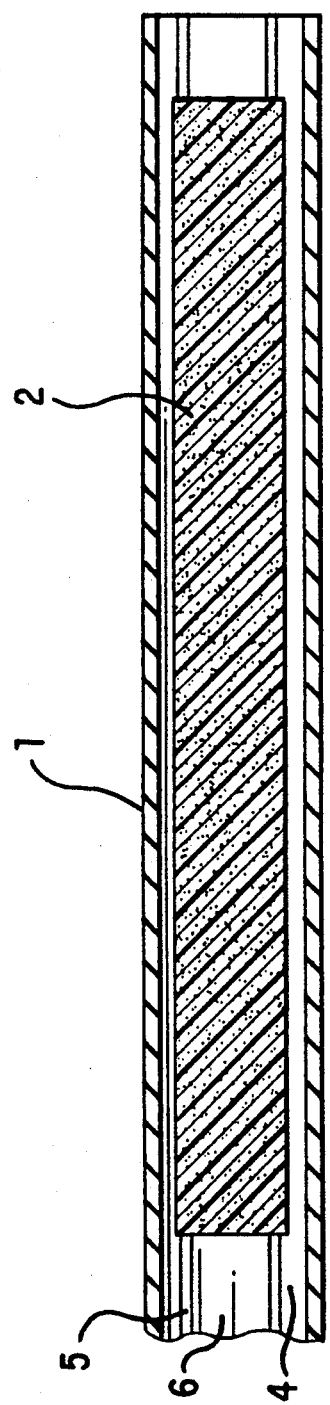
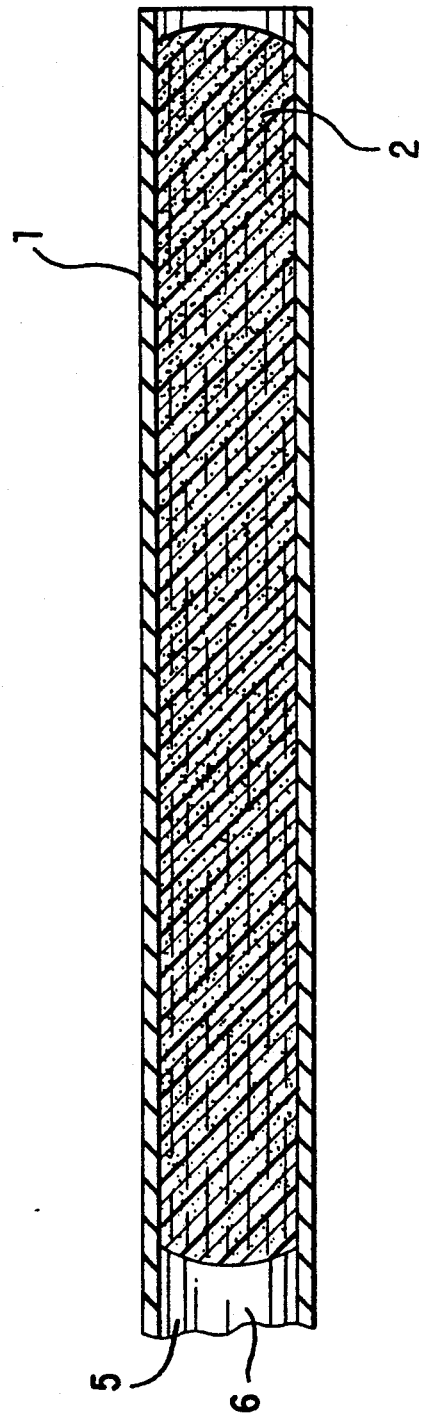
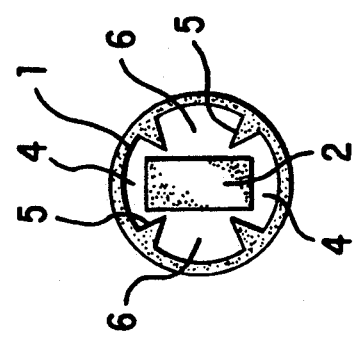
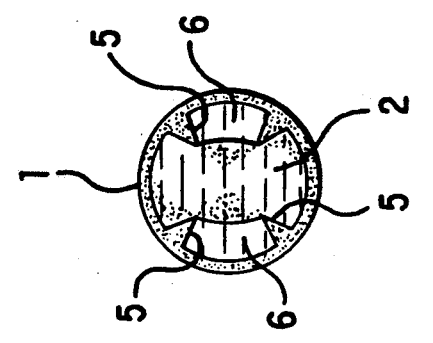

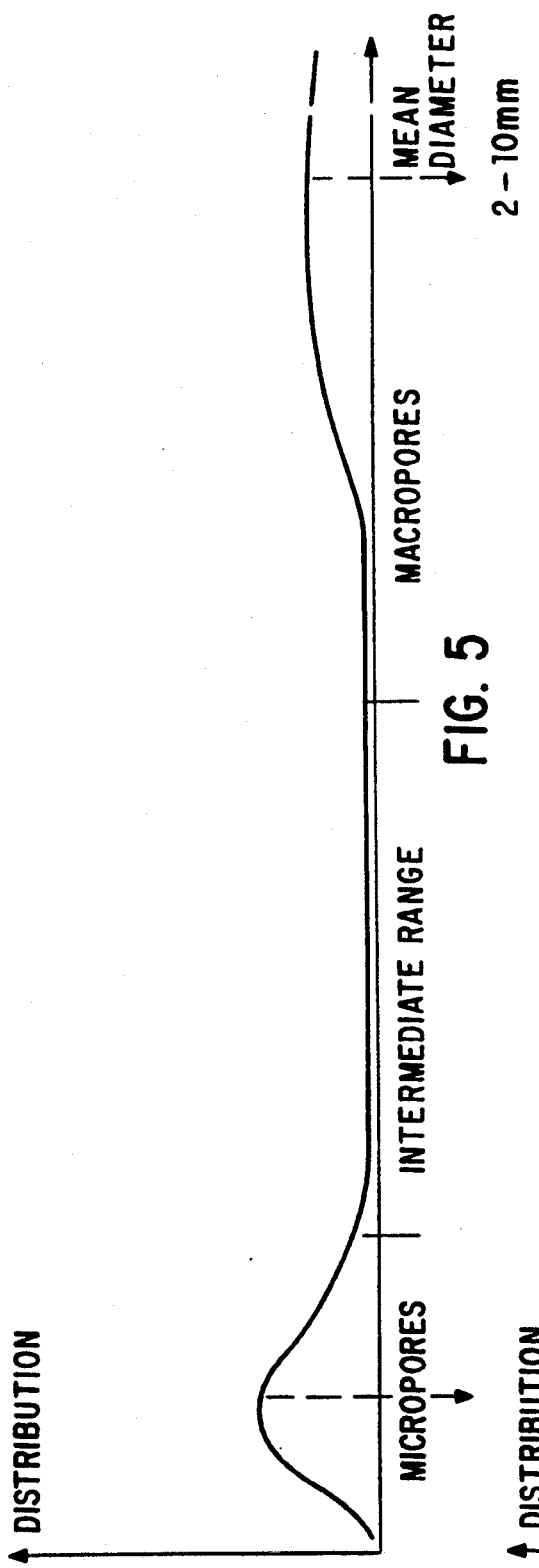
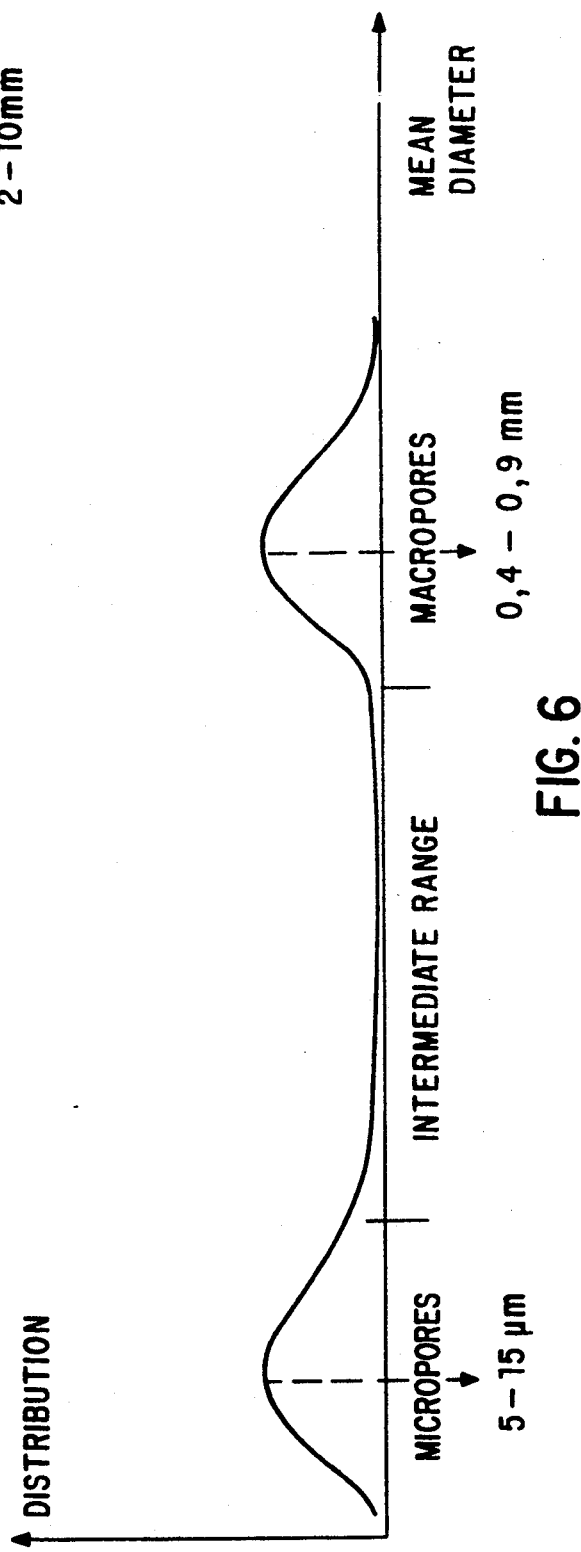
FIG. 5
FIG. 6

DEVICE FOR THE DETERMINATION OF INCISIONAL WOUND HEALING ABILITY

The present invention relates to a device and a method for the determination of the healing ability of an incisional wound or a connective tissue in man.

The tissue healing process begins within a matter of seconds from receiving a lesion or starting an operation and continues via blood coagulation and a highly diversified biological reaction chain towards connective tissue cicatrization. What in the beginning is a cell-abundant, slack and mechanically unstable tissue turns into a firmer and firmer tissue as days and weeks pass. Little by little the metabolism of this granulation tissue becomes slower. The shape, final size and microscopic texture of a cicatrix tissue are determined according to the patient's age, sex, general metabolism and local tissue strength requirement.

With animal experiments it has been possible to indicate that the amount of cells appearing in the wound area during the first days and the relative quantitative proportions thereof determine the course of healing for weeks onwards. Although it is possible with test animals to study the local healing rate of tissues in many different ways from the wound itself, this has not been possible with human beings Clinically estimated, the healing of tissues is either a success or a failure. No information has been obtainable from a closed incisional wound about the deceleration of healing and the reasons possibly contributing to this.

There is a prior known device and method for collecting wound cells from an incisional wound (Viljanto, J., J. Surg. Res. 20 (1979) p. 115-119). In this prior known method a thin silicone rubber tube with a cellulose sponge at one end is placed in the wound for picking up a sample of wound cells for analysis. An object of the present invention is to improve this device and method for providing a reliably operating, tissue-healing testing device as well as a method which is reliably reproducible and whereby the accuracy of analysis results is improved and their utilization is facilitated.

A device of the present invention for detecting wound healing ability comprises a flexible capillary tube inserted in a conventional manner into a wound, the tip of this tube left in the wound being fitted with a sponge for the attachment and growth of cells. A characterizing feature of this device of the invention is that at least that end of a capillary tube left inside the wound is provided with at least one inner groove and that the sponge is a wet-expanding viscose cellulose sponge, containing macro- and micropores in communication with each other. The inner design of a capillary tube according to the invention provides a firm attachment of the sponge to the end of a tube and at the same time there is secured the free entrance and movement for cell-containing wound exudate in the capillary tube and in the sponge. In a preferred embodiment, the interior of a capillary tube is divided into four substantially equal-sized grooves. This produces two opposite pairs of grooves having therebetween ridges retaining the piece of sponge.

The viscose cellulose sponge is preferably rectangular in cross-section and so dimensioned that, when dry, it extends from one groove of a capillary tube to the opposite groove, the side grooves remaining free even in the expanded condition of a viscose sponge, whereby the fluid is allowed a free flow in these free side grooves. The capillary tube is preferably made of silicone rubber.

The invention relates also to a method for the determination of incisional wound healing ability, wherein a sponge mounted on a capillary tube and intended for the attachment and growth of wound cells is inserted in a wound for sampling. This invention is characterized in that, after the sampling, the sponge is rinsed with a certain rinsing liquid, at a certain rinsing speed and with a certain amount of rinsing liquid, followed by treating the cell suspension in a per se known manner for differential counting of the cells and and comparing the obtained results with reference values.

The comparison is most preferably effected by means of a computer.

With a device of the invention it is possible to obtain already at the early stage of healing, usually after 48 hours, a representative cell specimen anticipating subsequent healing. By means of the further treatment and differential counting of cells it is possible to find out whether the healing of an examined patient's wound is proceeding as would be expected on the basis of his or her age and sex. If there is abnormality in the local cytological response at the early stage of healing, its clinical significance can be clarified in several cases. If the question is about a disturbance caused by the lack of nutrients or trace elements, it can be still be at least partially repaired during the course of healing.

It should be appreciated that the analysis of wound cells is not solely intended for anticipating the healing of a wound tested. The cytological response primarily reveals the responsive ability and strength of an examined individual over the entire healing process. It has been said that wound healing is an indicator of the vitality of a whole individual as it requires the coordinated combined effect of all blood cells, connective tissue cells as well as dozens of different enzymes, catalysts and intermediator substances.

In order to make a wound cell analysis reliably reproducible, a device collecting wound cells must be structurally standardized. This is particularly true regarding a cellulose sponge placed inside a slicone rubber tube. Cells are extremely sensitive to even slight changes in the surface texture and pore size of a sponge. Therefore, even microscopically studied, the sponge texture should be homogeneous and dimensionally precisely quantified.

The interpretation of a cellular analysis would not have been practically possible without data processing technology. A method of the invention facilitates the preparation of information obtained from a cellular analysis and suitable for clinical application within a matter of minutes from the moment the data is supplied from a computer terminal. Thereafter, it is possible to collect continuously increasing material for detecting disease-linked and hereditary effects on the healing of tissues.

Figure 2:
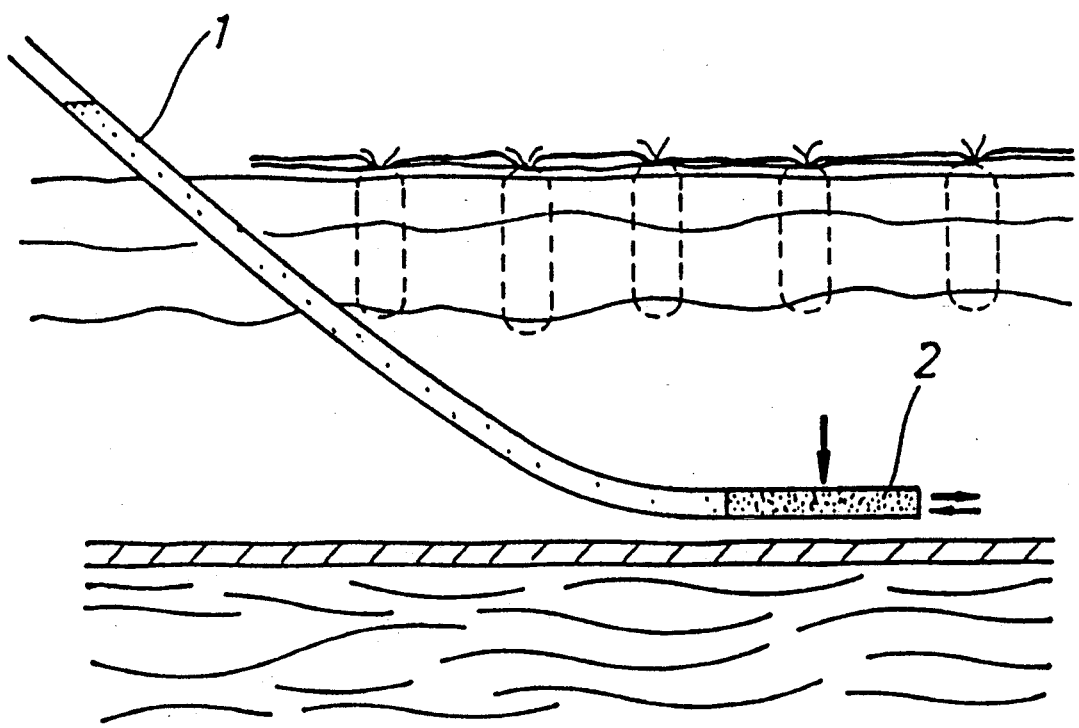

The invention will now be described in more detail with reference made to the accompanying drawings, in which FIG. 1 shows a device of the invention wrapped in a protective package, FIG. 2 shows a device of the invention implanted in a wound, FIGS. 3A and 3B show the sponge-facing end of a capillary tube as an enlarged longitudinal and crosswise section, FIGS. 4A and 4B show the same as FIGS. 3A and 3B but the sponge imbibed with fluid, FIGS. 5 and 6 show the distribution curves for macro- and micropores in a prior known sponge and in a sponge of the invention.

A device of the invention comprises a pliable capillary tube 1, which is preferably made of silicone rubber and one end of which is fitted with a wound cells collecting sponge 2. For the purpose of use, this tube 1 of the invention is packed in a transparent protective case 3, in which the capillary tube is fastened to a base sheet by means of protective films. For the purpose of application, the protective films can be readily torn off from the end of capillary tube 1 and, as shown in FIG. 1, a plurality of such capillary packages can be koined side by side and removed one by one.

A capillary tube 1 removed from the package is placed inside a wound as shown in FIG. 2. A capillary tube 1 is left in this position for e.g. 48 hours with fluid being collected in capillary tube 1 and absorbed in sponge 2.

It is important that the shape of capillary tube 1 and sponge 2 be such that said sponge 2 remains firmly in position also in an expanded condition. It is also important that wound fluid be able to flow freely in capillary tube 1 and the capillary tube not be blocked by expanded sponge 2. In a solution of the invention (FIGS. 3 and 4), the capillary tube is provided with at least one inner groove 4, 6. In the case shown in FIGS. 3 and 4, the number of grooves 4, 6 is four, comprising pairs of grooves 4, 6 disposed in opposite relation to each other. Thus, between the grooves there are formed ridges 5 pointing towards the centre of the tube.

A sponge 2 inserted in the end of tube 1 is rectangular in cross-section and so dimensioned that in a crosssection its opposite ends extend into the corresponding inner grooves 4 of a capillary tube leaving the other pair of inner grooves 6 vacant. In addition, sponge 2 is placed entirely in capillary tube 1 in a manner that, in an expanded condition, said sponge 2 does not extend out of capillary tube 1 (FIG. 4).

When this capillary tube 1 along with its sponge 2 is placed in a wound, the wound fluid has unhindered entry in capillary tube 1 by virtue of the side grooves 6 on either side of sponge 2. The ridges 5 between grooves 4, 6 prevent viscose sponge 2 from working its way into side grooves 6, which remain vacant and facilitate the flow of wound fluid in the capillary tube.

In order to achieve a preferred result, a viscose sponge 2 used must be as homogeneous as possible. It must contain both micro- and macropores which are in communication with each other so that wound cells are able to migrate from one pore to another. The sponge must also be clinically clean and so must the capillary tube. In this context, the macropores refer to pores whose diameter is in the order of 1.0 mm and the micropores refer to pores whose diameter or linear measure is in the order of 10 $\mu$m. Since the purpose of a sponge is to collect cells from a surgical wound and to offer them a natural culture medium, its texture is of prime importance in view of the invention and decisive in terms of the function of a viscose sponge. Important in view of the operation is a relative proportion between micro- and macropores, the correct size and shape of pores as well as the openings in the partitions of pores for facilitating the migration of cells from one pore to another.

When studying a human being, it is for practical reasons necessary to employ a small device and, thus, a viscose sponge used is also small. In order to achieve a preferred result, the viscose sponge used must be as homogeneous as possible. A requirement for this is that there will be as little fluctuations as possible in the pore size distribution of a sponge. The peaks of micro- and macropore distributions must be as narrow as possible, especially the presence of a very large macropore in sponge 2 would nullify the entire analysis process.

In the industrially produced sponges, the macropores have been too large in terms of proper functioning by preventing the attachment of cells to the walls of a pore and the macropore distribution has also been too wide (FIG. 5).

It is important in terms of proper functioning that micropores are as large as possible, distribution mean within the range of 5–15 $\mu$m, and macropores respectively as small as possible, distribution mean within the range of 0.4–0.9 mm (FIG. 6).

The manufacturing of a viscose cellulose sponge is known as such. Thus, the manufacturing of a micro- and macropores containing sponge of the invention proceeds according to prior known methods and can be effected e.g. as follows:

In fiber-containing special viscose are added screened sodium sulphate crystals under vacuum. Viscose is solidified and sodium sulphate crystals are removed by dissolving. The sponge is bleached and pressed, dried and cut into pieces of suitable size.

Following the sampling, the outer end of capillary tube 1 is attached to a rinsing device, wherein the sponge is rinsed for recovering the cells collected therein for analysis. In view of the functioning and reproducibility of the method it is important to employ a certain rinsing agent, rinsing speed and amount of rinsing liquid. When selecting these parameters, care should also be taken that the cells contained in the sponge do not break during the rinsing operation.

The results obtained in the studies are analyzed and these results are compared with values obtained earlier in similar tests. Due to an extensive and diversified comparison, this can only be practically performed by means of a computer, whereby the result is obtained almost immediately and necessary therapeutical measures can be initiated as quickly as possible.

Clinical Use of Cell sampling Device

At the end of an operation, prior to the closing of the skin wound, a cellulose sponge cut to a predetermined shape and size and fixed to one end of a silicone rubber tube, is imbibed with 0.9% saline, after which the sampling tube is inserted in the surgical wound in such a way that the open end of the tube is fastened under sterile conditions to the skin with tape.

The sampling tube is removed from the wound after a given time by pulling lightly. The open end of the sampling tube which was on the skin is attached for the rinsing of the sponge to a pump which delivers a constant volume e.g. 2 ml of isotonic citrate solution over a given period, generally 5 seconds. The rinsing liquid, the amount and rate of its supply are selected in such a manner that the cells can be removed from the surface and pores of the sponge without damaging the cells.

After rinsing, sample batches of equal size (200 $\mu$l) are taken from the cellular suspension and the samples are centrifuged in a cytocentrifuge at the speed of 1000 rpm for 7 minutes. The cells transferred to slides are air-dried, fixed in absolute ethanol and stained according to the May-Grünwald-Giemsa method in an automatic staining apparatus. From these stained slides is performed a differential count of the cells and the results obtained are compared with the reference material obtained from healthy operated patients.

The healing of the wound is considered normal when the so-called biological healing has progressed as far as the chronological time used for healing requires on a patient of a certain age. If the biological healing, which in this case is measured by the absolute amount of cells in the wound at each point of observation and by the relative proportion of each cell type, has not progressed to the stage required by the chronological healing time, then the healing of the wound has retarded. When biological healing progresses more rapidly than chronological healing, the healing of the wound is taking place more rapidly than average in the same age group. Using the method for determining the healing speed of a wound requires the existence of comprehensive reference material and its own adpprogram.

EXAMPLE

Let us suppose that the capillary sampling tube is removed 47.8 hours after its insertion into the wound. The chronological time used for healing is thus the same, that is, 47.8 hours. The cell content of the capillary sampling tube, which due to the special structure of this sampling tube corresponds to the type and relative amount of the cells in the surgical wound, is counted subsequent to MGG staining by means of conventional differential counting. The values obtained are fed from the computer terminal to be processed by the CELLCO adp-program and to be compared with the reference material. Each of the ten cell ratios indicates a particular healing time, some ratios more accurately than others. The predicted value of the cell ratios has been taken into account as weighted averages in the adpprogram. Let us suppose that the biological healing time obtained for an example patient is 44.7 hours. The difference between healing times, $-3.1$ hours, is more than $-2SD$ ($-2.4$ hours) and thus this difference can be considered significant and the healing of the wound on the example patient slower than average in the same age group. A closer comparison between cell ratios by means of an adp-program into "gates" calculated at 99% confidence limits gives in many cases also suggestive information of the primary reasons for the retardation. In some cases healing can then still be promoted by suitable post-operative treatment.

May it also be pointed out that the cell sample from a wound obtained by means of the sampling tube relating to the invention can, in addition to the foregoing, be studied by means of a variety of biomedical methods in order to solve the special problems relating to the recovery of the patient.

The most common implantation time is 48 hours. Shorter or longer periods can be employed, whereby the rinsing speed of a rinsing liquid changes accordingly. A sampling time of 24 hours requires a slower rinsing speed while a sampling time of 72 hours requires a faster supply speed.

We claim:

1. A device for collecting wound exudate from an incisional wound the device comprising a pliable capillary tube (1) to be left inside a wound, the tube end to be plaxed in a wound being fitted with a sponge (2) intended for the attachment and growth of cells, wherein at least the end of capillary tube (1) to be left in the wound is proved with at least one inner groove (4,6) and that the sponge is a wet-expanding viscose cellulose sponge containing macro- and micropores in communication with each other.

2. A device according to claim 1, wherein the distribution mean of micropores is within the range of 5–15 μm and the average distribution mean of the diameters of macropores is within the range of 0.4–0.9 mm.

3. A device according to claim 1, wherein the interior of capillary tube (1) is divided into four substantially equal-sized grooves (4, 6).

4. A device according to claim 2, wherein said sponge (2) is rectangular in cross-section and extends in capillary tube (1) from one groove (4) to the opposite groove (4), thus leaving side grooves (6) vacant also in an expanded condition of the sponge.

5. A device as in any of claim 1–4, wherein said capillary tube (1) is made of oxygen permeable silicone rubber.

* * * * *